United States Patent [19]

Allen

[11] Patent Number: 4,928,786

[45] Date of Patent: May 29, 1990

[54] SELF-SEALING DUAL STETHOSCOPE HEAD

[76] Inventor: Derek R. Allen, 30994 Steeplechase Dr., San Juan Capistrano, Calif. 92675

[21] Appl. No.: 340,667

[22] Filed: Apr. 20, 1989

[51] Int. Cl.[5] .......................... A61B 7/02; H04R 25/00
[52] U.S. Cl. ...................................... 181/137; 181/131
[58] Field of Search ................................. 181/131, 137

[56] References Cited

U.S. PATENT DOCUMENTS

| | | | |
|---|---|---|---|
| 3,712,409 | 1/1973 | Kizakisz et al. | 181/137 |
| 4,212,368 | 7/1980 | Allen | 181/131 |
| 4,823,906 | 4/1989 | Gabriel | 181/137 |

Primary Examiner—Benjamin R. Fuller
Attorney, Agent, or Firm—George F. Bethel; Patience K. Bethel

[57] ABSTRACT

A self-sealing dual stethoscope head including a low frequency sound receiving bell, a high frequency sound receiving diaphragm, a selectively movable valve including a cylindrical valve seat having a first acoustical passage in sound communication with the bell and a second acoustical passage in sound communication with the diaphragm, and a cylindrical valve member having a radial opening for selective alignment and sound communication with the bell acoustical passage or the diaphragm acoustical passage upon rotation thereof, the cylindrical valve member being characterized by having at least a portion of an arcuate lengthwise segment of diminished radius as compared to the remaining lengthwise portion of the cylindrical valve member, means for urging the cylindrical valve member into sound sealing contact with the first or second acoustical passages within the valve seat and means for locking the cylindrical valve members into position during alignment with an acoustical passage.

17 Claims, 2 Drawing Sheets

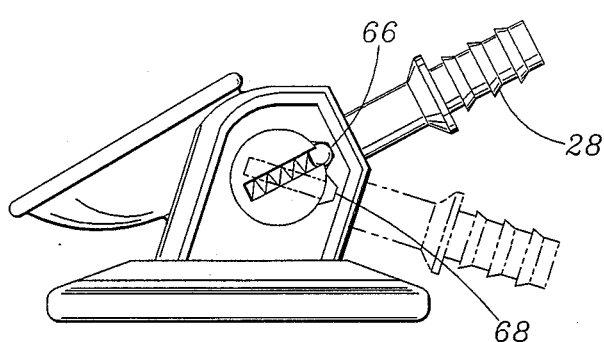
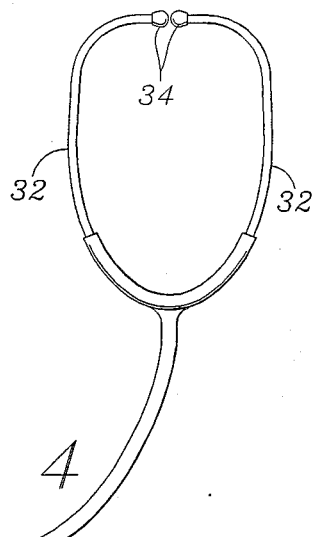
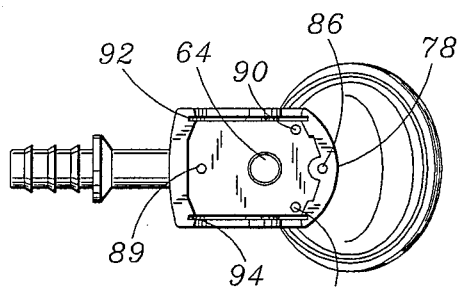
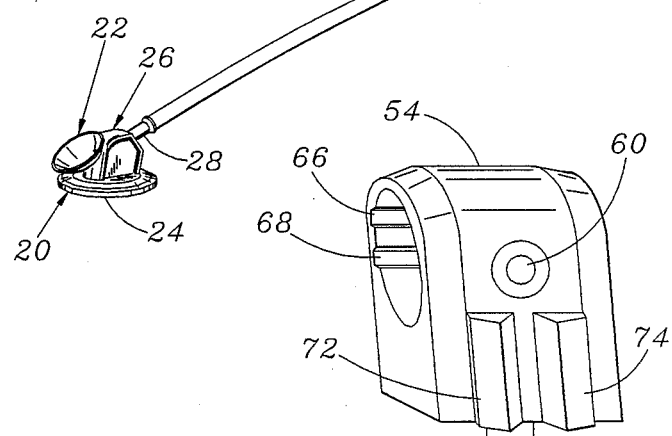
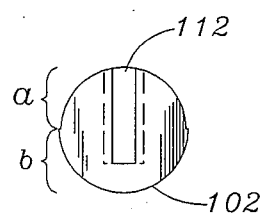
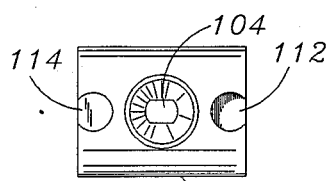
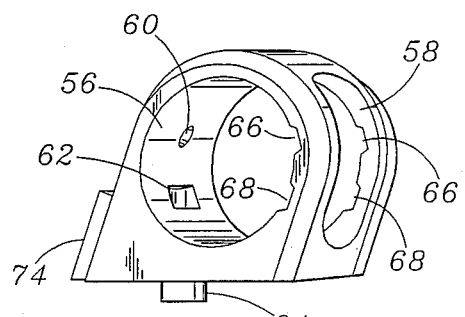

SELF-SEALING DUAL STETHOSCOPE HEAD

FIELD OF THE INVENTION

This invention relates to the field of stethoscopes, and especially to a dual stethoscope head having a bell and a diaphragm with a selectively movable self-sealing valve connecting the bell and the diaphragm.

DESCRIPTION OF THE PRIOR ART

In my prior patent U.S. Pat. No. 4,212,368 I have disclosed and claimed a dual stethoscope head having a low frequency sound receiving bell and a high frequency sound receiving diaphragm. The bell is offset from the diaphragm axis. The bell axis intersects the diaphragm axis at an acute angle. A selectively movable valve in the form of a cylindrical valve member is rotated to acoustically connect the bell and the diaphragm, individually, to an airway which is connected to a sound tube leading to binaurals. The cylindrical valve member is seated and totally supported within a cylindrical bore in the head body.

An airway or sound tube is connected to the valve member allowing the passage of acoustical waves through the valve member of the tube leading to the binaurals. The airway or sound tube also acts as a lever to facilitate rotation of the valve member between predetermined limits in which the latter is in acoustic communication with the bell or the diaphragm. This is facilitated by movement of the hand of a user to rotate the valve member between the bell or the diaphragm. The valve member is also provided with a means to lock the valve member in the position in which the acoustical passageways are joined.

For proper operation of the dual stethoscope head thus described, the valve member must be very closely sealed to its valve seat in order to eliminate acoustical leaks and sound transmission defects within the instrument. This requires very close tolerances between the valve member and the valve seat increasing the cost of manufacture. Also, it is necessary to additionally provide a high temperature valve grease such as high-melt silicone grease to further seal the valve to the valve seat.

It is an object of the invention to provide a more efficient means to seal the valve member within the valve seat.

It is a further object of the invention to provide a means for sealing the valve member within the valve seat which is less expensive to manufacture requiring reduced tolerances between the valve member and the valve seat.

SUMMARY OF THE INVENTION

The novel dual stethoscope head of the invention, including a low frequency sound receiving bell and a high frequency sound receiving diaphragm, includes a selectively movable valve in the form of a cylindrical valve member which is seated and totally supported within a cylindrical bore in the head body. The cylindrical bore or valve seat is provided with a first acoustical passage in sound communication with the bell and a second acoustical passage in sound communication with the diaphragm.

The cylindrical valve member is provided with a conduit or channel for the passage of air and sound which is disposed intermediate the ends and perpendicular to the cylindrical axis. An airway tube is connected to the conduit or channel at one end and at its opposite end to a sound tube leading to the binaurals. The airway tube acts as a lever to facilitate rotation of the valve in order to align the cylindrical valve member conduit and provide acoustic communication with the bell or the diaphragm depending on its location. The cylindrical valve member contains means in the form of slots for containing a spring and ball which permit the selective locking of the valve conduit in sound communication with either the bell or the diaphragm upon movement of the airway tube and seating of the balls within grooves or indentations within the cylindrical valve bore or seat.

The novelty of the invention lies primarily in the shape of the cylindrical valve member. In my prior application the cylindrical valve is of uniform diameter. In the new cylindrical valve member described and claimed in this invention, when viewed along its cross-section, the radius describing an arc segment of 180° and forming one lengthwise half of the cylinder is just slightly greater than the radius describing an arc segment of 180° and forming the remaining contiguous lengthwise half of the cylindrical member.

A major advantage of this design is to provide an effective air seal without extensive machining. The half of the cylindrical valve member having the greater radius falls by gravity and by the urging of the spring and ball snugly into the bottom portion of the valve seat in the area bounded by the first and second acoustical passages in sound communication with the bell and the diaphragm. The diminished radius half provides the needed rotational clearance for easy insertion and rotation of the valve in its seat.

This is made possible by the fact that the valve seat in the form of a cylindrical bore is engineered and machined to be slightly greater in diameter than twice the radius of the valve cylinder half having the larger radius.

The valve cylinder member lengthwise half having the larger radius is tightly held against the valve seat by means of a spring and ball which are held in a slot in either end of the valve cylinder. The valve seat contains a pair of lengthwise grooves or depressions into which a spring and ball are seated. When the balls are positioned within one of the channels, the conduit or channel within the cylindrical valve member is aligned with the bell acoustical passage and when the balls are accommodated in the other groove by movement of the airway tube, the cylindrical valve conduit or channel is aligned with the acoustical passage of the diaphragm.

The balls, in combination with the spring, tightly press the cylindrical valve member against the valve seat to create an effective air seal. This is made possible by the fact that the ball and spring press in a perpendicular direction on the axis in the direction in which you are trying to seal.

The air tube which is connected to the cylindrical valve conduit acts as a switch to allow the use of one hand for switching from one microphone mode to the other.

The self-sealing dual stethoscope in the invention is also designed wherein the diaphragm plate is separate from the switch which permits the manufacture of the diaphragm in plastic.

The invention will be more readily understood by reference to the following drawings taken in connection with the detailed description.

BRIEF DESCRIPTION OF THE DRAWINGS

FIG. 3 shows a side elevation of the stethoscope of the invention illustrating the two positions of the cylindrical valve;

FIG. 4 shows a perspective view of the stethoscope of the invention attached to binaural tubes;

FIG. 5 shows the underside of the valve assembly;

FIG. 6 shows a length-wise view of the cylindrical valve member;

FIG. 7 shows a perspective view of the cylindrical valve seat;

FIG. 8 shows a different perspective view of the cylindrical valve seat; and,

FIG. 9 shows an end view of the cylindrical valve member of FIG. 6 detailing the difference in radius between the two lengthwise halves of the cylindrical valve member.

DESCRIPTION OF THE PREFERRED EMBODIMENTS

Figures 1, 2:
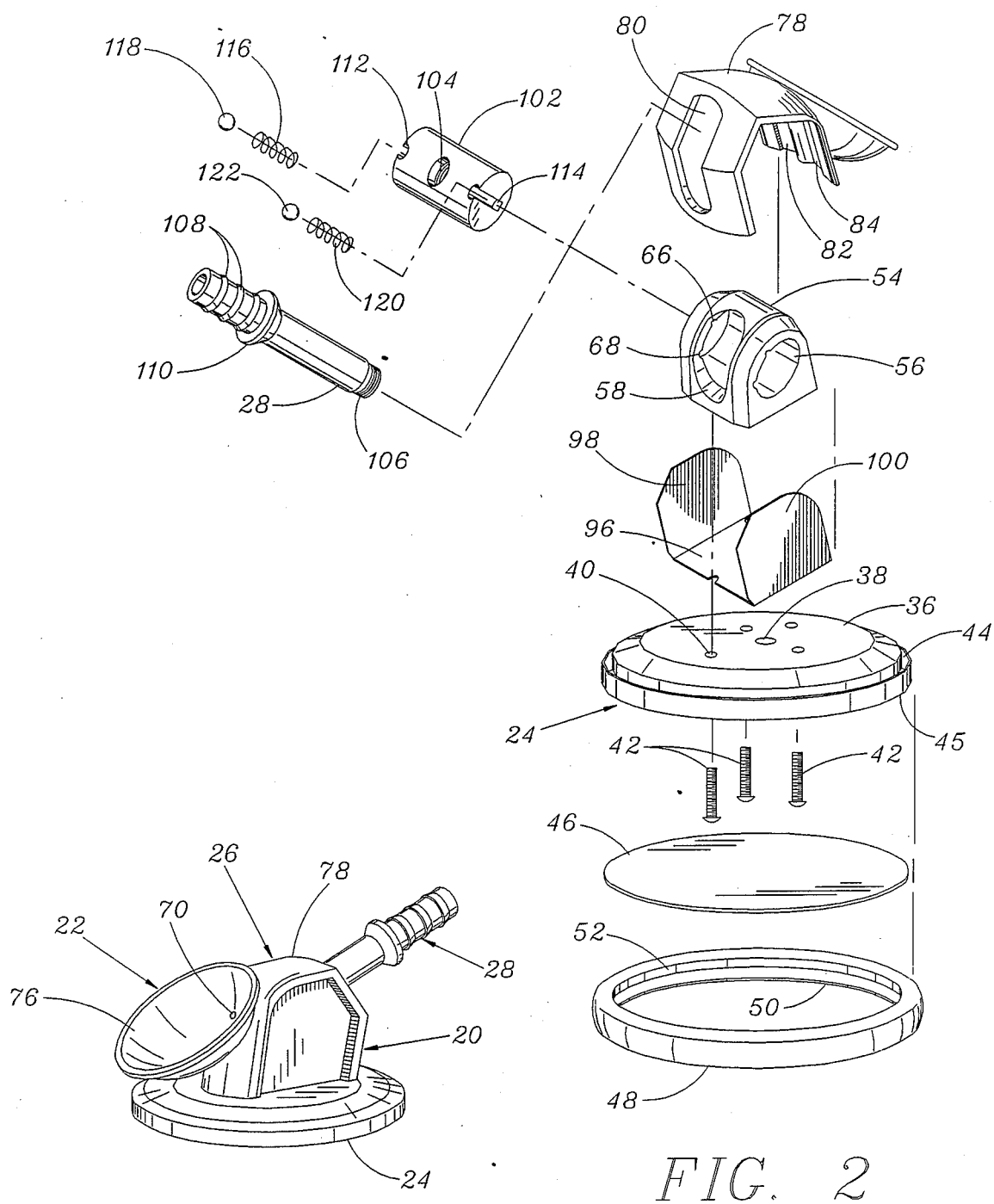
FIG. 1 is a perspective view of the stethoscope of the invention.
FIG. 2 is an exploded view of the separate elements included in the invention in order to show the structural relationships of the preferred embodiment.

As shown in FIGS. 1 and 4, a stethoscope head 20 includes a low frequency sound receiving bell 22 and a diaphragm assembly 24 for reception of high frequency sound attached to a valve assembly 26. An airway tube 28 connected at one end to the valve assembly 26 is also connected to a sound tube 30 at its opposite end which communicates with binaurals 32 which are connected to eartips 34.

The separated parts of the stethoscope head 20 can be seen in an exploded view in FIG. 2. Here it can be seen that the diaphragm assembly 24 includes a plate 36 having an acoustical air passage 38 and interiorly threaded holes 40 for receiving screws 42 for attachment to the body member 54 of the valve assembly 26.

The diaphragm plate 36 is provided with a flange 45 and a shoulder 44 which surrounds the diaphragm plate 36. The diaphragm 46 in the form of a plastic disk is held against the bottom of the diaphragm plate 36 by means of an O-ring 48. The O-ring 48 includes an interior peripheral channel 50 and an interior peripheral flange 52. The peripheral flange 52 seats on the shoulder 44 of the diaphragm plate 36 while the flange 45 of the diaphragm plate 36 and the diaphragm 46 are seated within channel 50 of O-ring gasket 48.

The valve assembly 26 is detailed in FIGS. 2 and 5-9. As shown particularly in FIGS. 7 and 8, a body member 54 has a substantially cylindrical central bore 56 which acts as a valve seat. A side opening 58 communicates with the cylindrical valve seat 56 for accommodation and movement of the air lever tube 28.

As shown in FIG. 8, within the cylindrical valve seat 56 there are provided a first air acoustical passage 60 which communicates with the bell 22 and a second acoustical passage 62 which communicates acoustically with the diaphragm assembly 24. With reference to FIG. 2, it can be seen that the acoustical passage 62 projects at 64 from the body member 54 for insertion into aperture 38 of diaphragm plate 36 as indicated in FIG. 2.

The valve seat 56 as shown in FIGS. 7 and 8 is provided with a pair of length-wise channels 66 and 68.

The body member 54 is also provided with a pair of exterior upstanding ridges or length wise protrusions 72 and 74. Preferably, the body member 54 is cast as a one-piece member.

As shown in detail in FIGS. 2, 3, and 5, the bell assembly 22 includes a bell 76 in the form of a generally concave cross-sectional configuration forming a bowl-like member. The bell 76 has an aperture 70 for acoustical communication with first acoustical passage 60 of member 54. The bell is preferably made integrally with a substantially U-shaped body member 78. As shown in some detail in FIG. 2, the U-shaped body member 78 includes a central passage 80 for alignment with opening 58 of member 54 and a pair of interior channels 82 and 84 into which lengthwise projections or shoulders 74 and 72 of member 54 are seated.

As shown in FIG. 5, the underside of the assembled bell 76 and U-shaped body member 78 over the valve body member 54 also shows an interior threaded aperture 86. The underside of the body member 54 is also shown and includes the projection 64 and three interiorly-threaded bores 88, 89, and 90. The U-shaped body member 78 also includes a U-shaped slot 92 and another U-shaped slot 94 for accommodation of sleeve member 96 having upstanding sides 98 and 100 which slip into respective slots 94 and 92 of U-shaped body member 78 to enclose the cylindrical valve member 102 within the cylindrical valve seat 56.

The valve assembly 26 will now be described in detail. As shown in FIG. 2, 6, and 9, the cylindrical valve is in the form of a valve cylinder 102 having a radial side wall conduit or channel 104 which passes radially in a perpendicular direction through the axial center of the cylinder intermediate the ends. The conduit or channel 104 acts as an acoustical passage for alignment with acoustical passages 60 and 62 within the valve seat 56.

The conduit or channel 104 is internally threaded for receiving air tube lever 28 which has an exteriorly threaded end 106. Air tube lever 28 also includes at its opposite end a plurality of exterior ridges or flanges 108 and a stop in the form of a shoulder 110. The ridges 108 permit the slip-fit and sound sealing of a rubber sound tube 30 there over.

The cylindrical valve member 102 also includes end wise radial slots 112 and 114 which are aligned parallel with conduit or channel 104 and pass radially in a perpendicular direction through the central axis of the valve cylinder member 102. The slots 112 and 114 do not pass completely through the valve cylinder member 102.

Slot 112 accommodates a spring 116 and a ball 118 and similarly, slot 114 accommodates spring 120 and ball 122.

A particularly novel feature of the invention lies in the cylindrical valve member 102 as shown in FIG. 9. The end-wise view shown indicates that the radius of the lengthwise half of the valve 102 as indicated at A is slightly less than the radius of the adjacent length wise half of the valve as indicated at B.

While the valve seat 56 is configured to accommodate a cylinder of diameter slightly greater than twice that of radius B, the advantage of the invention lies in the fact that having a slightly smaller circumference in the lengthwise half as shown in A permits the easy rotation of the cylindrical valve 102 within the valve seat 56 while at the same time effectively sound sealing the valve.

As shown, the lengthwise half as indicated at B having the larger radius is aligned with the portion of the valve seat 56 which includes the acoustical passages 60 and 62. The lengthwise half of the valve as indicated at A having a lesser radius is aligned with the portion of the valve seat 56 having the central opening 58 and having the lengthwise grooves 66 and 68. The very slight difference in radius of lengthwise portion A of the cylindrical valve as compared to the lengthwise portion B permits the easy rotation within the valve seat 56.

The presence of the springs 116 and 120 and the balls 118 and 122 which fit respectively in slots 112 and 114 urge the larger radius lengthwise portion B of the valve member 102 tightly against the valve seat 56 in the vicinity of the acoustical passages 60 and 62. This provides a tight fit which effectively sound seals the cylindrical valve member conduit or channel 104 against the acoustical passages 60 and 62.

As can be seen in FIG. 3 the air tube 28 is selectively locked into position by movement of the air tube lever 28 between the two channels 66 and 68 within the valve seat 56 which locks the balls 118 and 122 into the respective grooves 66 or 68. This action tightly sound seals the conduit or channel 104 in valve cylinder member 102 and the air tube 28 in alignment with either the acoustical passage 62 as indicated in FIG. 3 or with the acoustical passage 60 as shown in outline in FIG. 3.

Thus, the slight differences in radius between the two respective lengthwise halves of the cylindrical valve member 102 permit the self-sealing aspects of the valve assembly of the invention. As an example, the radius B as shown in FIG. 9 can be 0.250 inch while the radius A as shown in FIG. 9 can be 0.242 inch. Thus the difference between the respective radius A and B is 0.008 inch. This small difference is sufficient to provide ease and rotation within the valve seat 56 as indicated in FIG. 8 which has an inside diameter of 0.503 inch.

It is important to note that the portion of the cylindrical valve member 102 having the larger radius B is the section which seals against the acoustical air passages 60 and 62 within the valve seat 56. The springs 116 and 120 in conjunction with the balls 118 and 122 keep the lengthwise section of valve member 102 as indicated in B tightly pressed against the valve seat 56.

This enables the effective sound sealing which is an improvement over prior art valve assemblies which would require valve lubricants to produce a less effective sound seal between the diaphragm or bell and the radial conduit within the cylindrical valve member 102.

Various modifications of the invention are contemplated and can be resorted to by those skilled in the art without departing from the spirit and scope of the invention as defined in the following appended claims.

I claim:

1. A self-sealing dual stethoscope head comprising:
   a low frequency sound receiving bell;
   a high frequency sound receiving diaphragm;
   a selectively movable valve assembly comprising a valve housing having a cylindrical bore valve seat having an axis and an interior surface;
   a first acoustical passage within said valve housing which opens into said interior surface of said cylindrical bore for sound communication with said bell;
   a second acoustical passage within said valve housing which opens into said interior surface of said cylindrical bore for sound communication with said diaphragm;
   a substantially cylindrical valve having an axis, two ends, and an exterior surface, said valve being seated within said cylindrical bore and having a channel therein for selective alignment and sound communication with said first acoustical passage or with said second acoustical passage upon rotation of said cylindrical valve within said cylindrical bore;
   means connected to said cylindrical valve for selectively moving said cylindrical valve between said first and said second acoustical passages; and,
   said substantially cylindrical valve comprising a first lengthwise accurate segment which has a radius sized to conform with and closely contact said interior surface of said cylindrical bore; and, said cylindrical valve further comprising a second lengthwise accurate segment which has a radius sized to avoid close contact with said interior surface of said cylindrical bore.

2. A stethoscope head as claimed in claim 1 wherein:
   said cylindrical bore has a substantially uniform diameter.

3. A stethoscope head as claimed in claim 2 wherein said cylindrical valve channel passes radially through said axis of said cylindrical valve to act as a sound channel for selective acoustical communication with said bell or said diaphragm; and,
   means within said cylindrical valve assembly for urging said first lengthwise arcuate segment of said cylindrical valve into sound sealing contact with said cylindrical bore when said conduit is aligned with said first or second acoustical passage within said cylindrical bore.

4. A stethoscope head as claimed in claim 3 wherein said cylindrical bore valve seat further comprises:
   a side wall opening within said cylindrical bore substantially opposite said first and second acoustical passages for accommodation of said means connected to said cylindrical valve for selectively moving said cylindrical valve channel between said first and said second acoustical passages.

5. A stethoscope head as claimed in claim 4 wherein:
   said means for selectively moving said cylindrical valve between said first and said second acoustical passages comprises a section of a hollow tube having two ends with means at one end for attachment to said cylindrical valve channel and means at the other end for attachment to a sound tube.

6. A stethoscope head as claimed in claim 3 wherein said urging means comprises:
   at least one radial slot within at least one end of said cylindrical valve which slot is substantially parallel with said cylindrical valve channel; and,
   at least one spring disposed within said slot.

7. A stethoscope head as claimed in claim 6 wherein said urging means further comprises:
   a pair of lengthwise grooves within said interior surface of said cylindrical bore which are substantially parallel with said axis of said cylindrical bore and disposed substantially opposite said acoustical passages;
   a ball disposed on said spring within said radial slot of said cylindrical valve for contact with said interior surface of said cylindrical bore so that said spring locks said ball within one of said lengthwise grooves when said channel within said cylindrical valve is aligned with said first acoustical passage and is locked within the other lengthwise groove when said channel within said cylindrical valve is aligned with said second acoustical passage upon movement of said means for selectively moving said cylindrical valve member.

8. A self-sealing stethoscope head comprising:
a first body portion including a low frequency sound receiving bell, said first body portion having an acoustical passage within said first body portion in sound communication with said bell;
a second body portion disposed within said first body portion, said second body portion having a cylindrical bore having an axis and an interior surface disposed there through and a substantially cylindrical valve having an axis, two ends, and an exterior surface which is seated and supported within said cylindrical bore to form a selectively movable valve assembly;
a third body portion comprising a diaphragm plate and a diaphragm, said diaphragm plate having an acoustical passage in sound communication with said diaphragm;
said cylindrical bore within said second body portion having a first acoustical passage in communication with said acoustical passage within said first body portion for sound communication with aid bell, and a second acoustical passage in communication with said acoustical passage within said diaphragm plate for sound communication with said diaphragm;
said substantially cylindrical valve within said second body portion having a radial channel to act as a sound tube for selective alignment with said first or said second acoustical passage within said cylindrical bore upon movement of said cylindrical valve;
means connected to said cylindrical valve for selectively moving said cylindrical valve between said first and said second acoustical passages;
said substantially cylindrical valve comprising a first lengthwise arcuate segment which has a radius sized to conform with and closely contract said interior surface of said cylindrical bore; and said cylindrical valve further comprising a second lengthwise arcuate segment which has a radius sized to avoid close contact with said interior surface of said cylindrical bore; and,
means for securement of said first, second and third body portions.

9. A stethoscope as claimed in claim 8 wherein:
said bell is integrally formed with said first body portion.

10. A stethoscope as claimed in claim 8 further comprising:
means within said valve assembly disposed within said second body portion for urging said cylindrical valve channel into sound sealing contact with said first or second acoustical passage within said cylindrical bore.

11. A stethoscope as claimed in claim 10 wherein:
said substantially cylindrical valve further comprises at least one radial slot within at least one end of said substantially cylindrical valve which accommodates a spring and a ball for urging said cylindrical valve channel into sound sealing contact with said first or second acoustical passage.

12. A stethoscope as claimed in claim 11 comprising:
a hollow tubular member attached to said substantially cylindrical valve channel to provide sound communication with said bell or said diaphragm through said first or second acoustical passage respectively;
at least two depressions within said cylindrical bore interior surface for selectively locking said ball into one of said depressions for sound sealing communication between said valve channel and said first or second acoustical passage upon movement of said hollow tubular member; and,
an opening within said first and said second body portions for accommodating movement of said hollow tubular member.

13. A stethoscope as claimed in claim 8 wherein said first, second, and third body portions are detachably secured together.

14. A stethoscope as claimed in claim 12 wherein said channel within said cylindrical valve is disposed intermediate the ends of said substantially cylindrical valve.

15. A stethoscope as claimed in claim 11 wherein there are two radial slots, one slot of which is disposed within each end of said cylindrical valve.

16. A self sealing valve comprising:
a valve housing having an interior region and an exterior region and having a cylindrical bore therethrough, said cylindrical bore having an axis, an interior surface and having at least one passage through said valve housing which opens into said interior surface of said bore which is in communication with said exterior region of said valve housing;
a substantially cylindrical valve having an axis, two ends, and an exterior surface which is seated within said cylindrical bore and having at least one channel within said substantially cylindrical valve for alignment with said passage within said cylindrical bore upon movement of said substantially cylindrical valve;
said substantially cylindrical valve comprising a first lengthwise arcuate segment which has a radius sized to conform with and closely contact said interior surface of said cylindrical bore; and said cylindrical valve further comprising a second lengthwise arcuate segment which has a radius sized to avoid close contact with said interior surface of said cylindrical bore; and,
means within said substantially cylindrical valve and said cylindrical bore for urging said cylindrical valve channel into sealing contact with said passage.

17. A valve as claimed in claim 16 wherein:
said channel passes radially through said axis of said substantially cylindrical valve for communication with said passage.

* * * * *